United States Patent
Witt et al.

(10) Patent No.: US 7,108,695 B2
(45) Date of Patent: Sep. 19, 2006

(54) FEEDBACK CONTROL IN AN ULTRASONIC SURGICAL INSTRUMENT FOR IMPROVED TISSUE EFFECTS

(75) Inventors: David A. Witt, Maineville, OH (US); Jerome R. Morgan, Norwood, OH (US); Foster B. Stulen, Mason, OH (US); James R. Giordano, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 237 days.

(21) Appl. No.: 10/197,794

(22) Filed: Jul. 18, 2002

(65) Prior Publication Data

US 2002/0183774 A1    Dec. 5, 2002

Related U.S. Application Data

(63) Continuation of application No. 09/573,650, filed on May 18, 2000, now Pat. No. 6,454,781.

(60) Provisional application No. 60/136,106, filed on May 26, 1999.

(51) Int. Cl.
*A61B 18/18* (2006.01)
*A61B 17/32* (2006.01)

(52) U.S. Cl. ......................... 606/41; 606/167

(58) Field of Classification Search ............ 606/37–40, 606/169; 600/474, 411, 437–471
See application file for complete search history.

(56) References Cited

U.S. PATENT DOCUMENTS

| | | | | |
|---|---|---|---|---|
| 3,885,569 A | * | 5/1975 | Judson | 606/37 |
| 5,322,055 A | | 6/1994 | Davison et al. | |
| 5,443,463 A | * | 8/1995 | Stern et al. | 606/51 |
| 5,707,369 A | | 1/1998 | Vaitekunas et al. | |
| 5,776,130 A | * | 7/1998 | Buysse et al. | 606/48 |
| 6,123,702 A | * | 9/2000 | Swanson et al. | 606/34 |
| 6,129,735 A | | 10/2000 | Okada et al. | |
| 6,139,561 A | | 10/2000 | Shibata et al. | |
| 6,325,811 B1 | * | 12/2001 | Messerly | 606/169 |
| 6,773,444 B1 | * | 8/2004 | Messerly | 606/169 |

FOREIGN PATENT DOCUMENTS

WO   WO 97/43967   * 11/1997 ................. 606/37

* cited by examiner

*Primary Examiner*—(Jackie) Tan-Uyen T. Ho
(74) *Attorney, Agent, or Firm*—Verne E. Kreger

(57) ABSTRACT

A temperature monitoring device and/or method which control the tissue temperature at the end-effector of a therapeutic ultrasonic cutting and coagulating instrument as the tissue is being heated with ultrasonic vibrations from the end-effector. One or more temperature sensors are located at the end-effector, preferably on a clamping member. The temperature sensors measure the temperature of the tissue engaged by the end-effector either directly or indirectly. An alternate method and apparatus provides an electrical tissue impedance measure in combination with an ultrasonic cutting and coagulating instrument to provide active feedback control of an ultrasonic generator.

7 Claims, 12 Drawing Sheets

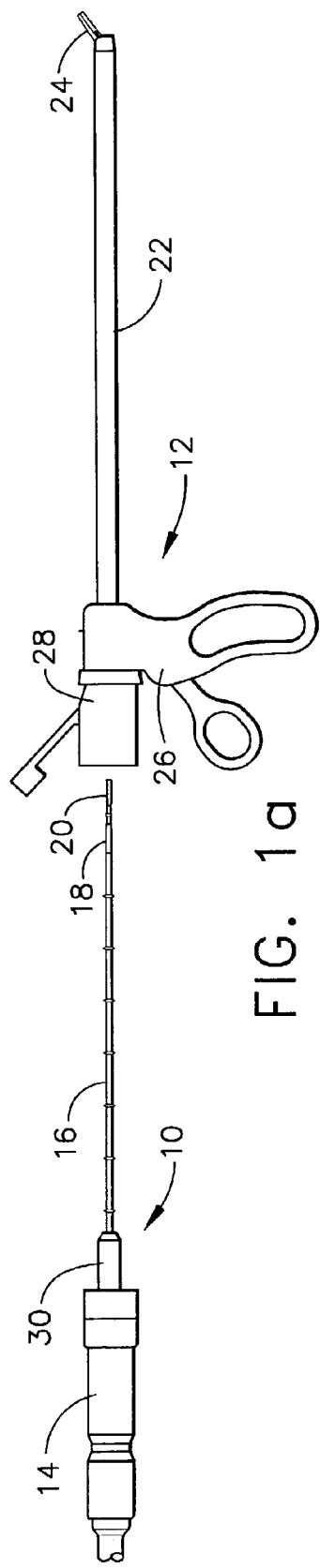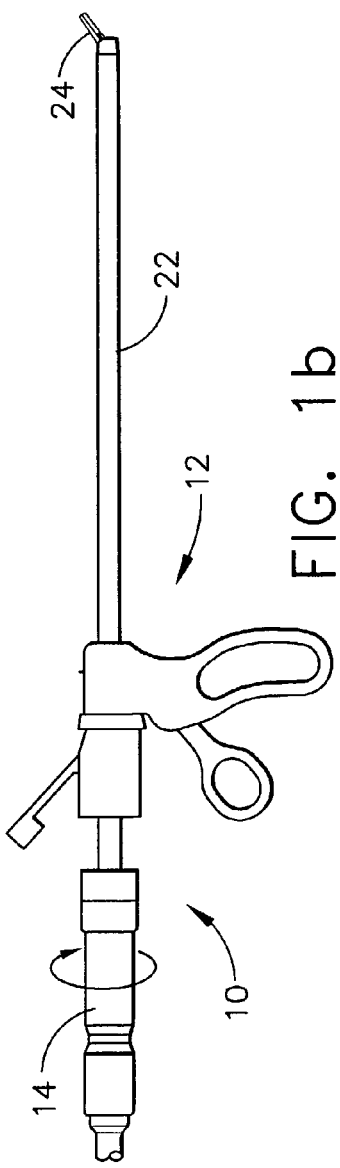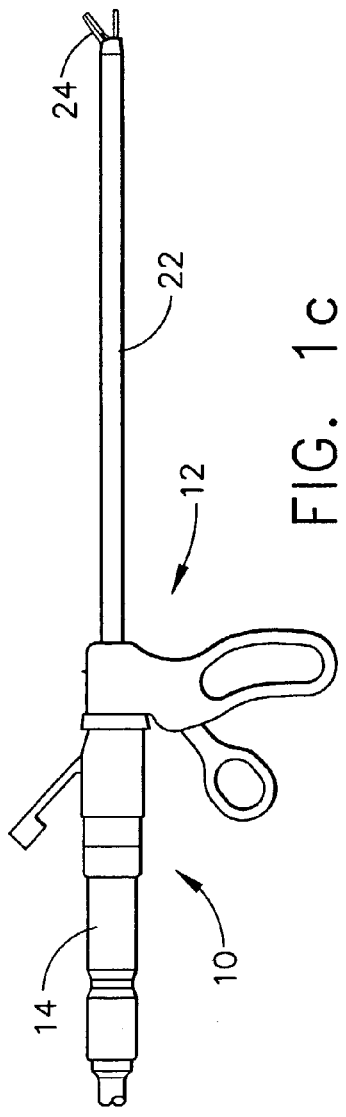

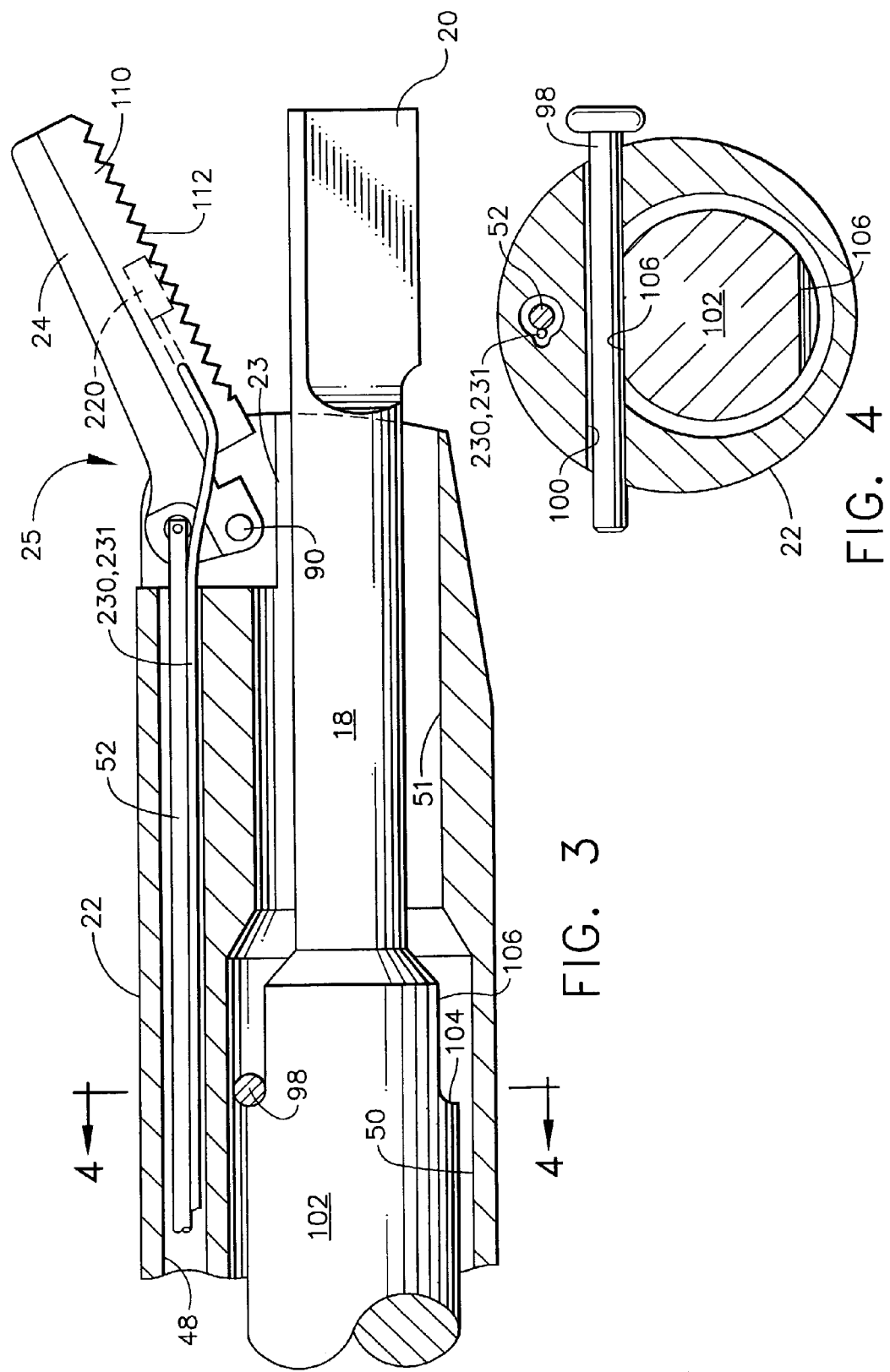

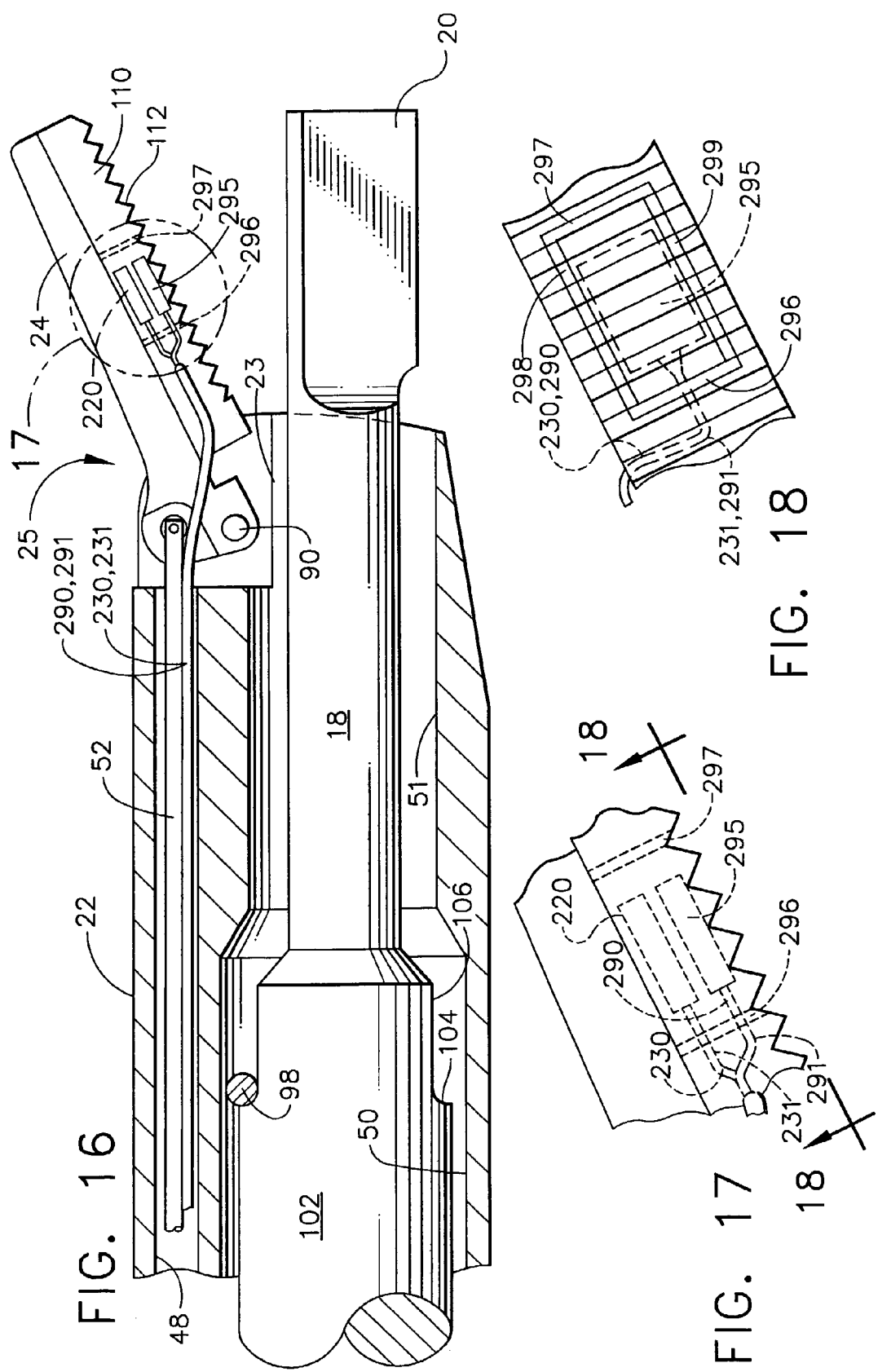

FEEDBACK CONTROL IN AN ULTRASONIC SURGICAL INSTRUMENT FOR IMPROVED TISSUE EFFECTS

CROSS REFERENCE TO RELATED PATENT APPLICATIONS

This application is a continuation of U.S. patent application Ser. No. 09/573,650, filed on May 18, 2000, now U.S. Pat. No. 6,454,781 B1, which claims the benefit of U.S. Provisional application No. 60/136,106 filed on May 26, 1999, both of which are incorporated herein by reference.

FIELD OF THE INVENTION

The present invention relates, in general, to an ultrasonic surgical device for cutting and coagulating tissue that utilizes closed-loop feedback and, more particularly, to a control method and apparatus for controlling the heat treatment of tissue in separate modes for ultrasonic cutting and ultrasonic coagulation.

BACKGROUND OF THE INVENTION

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, may be used to cut, dissect, or cauterize tissue. Ultrasonic instruments utilizing solid core technology are particularly advantageous because of the amount of ultrasonic energy that may be transmitted from the ultrasonic transducer through the waveguide to the surgical end-effector. Such instruments are particularly suited for use in minimally invasive procedures, such as endoscopic or laparoscopic procedures, wherein the end-effector is passed through a trocar to reach the surgical site.

Ultrasonic vibration is induced in the surgical end-effector by, for example, electrically exciting a transducer which may be constructed of one or more piezoelectric or magnetostrictive elements in the instrument hand-piece. Vibrations generated by the transducer section are transmitted to the surgical end-effector via an ultrasonic waveguide extending from the transducer section to the surgical end-effector.

U.S. Pat. No. 5,322,055 describes an ultrasonic surgical apparatus that includes a surgical instrument having a transducer for converting an electrical signal into longitudinal vibratory motion. The longitudinal vibratory motion is transmitted to an ultrasonic blade that is connected to the hand-piece. An accessory is releasably connected to the hand-piece to enable clamping of tissue against the vibrating blade to afford improved coagulating and cutting of tissue. In U.S. Pat. No. 5,322,055 scissors-like grips actuate a pivoted clamp jaw along one side of the ultrasonically vibrating blade to compress and bias tissue against the blade in a direction which is substantially normal to the direction of longitudinal vibratory motion.

Hemostatic devices have been described in various instruments for cutting, cauterization, coagulation or tissue welding. Most of the devices used are either monopolar or bipolar, for example, bipolar forceps, monopolar or bipolar scissors, and cutting and coagulating devices. See, for example, U.S. Pat. No. 5,707,369 that describes a temperature feedback system for closed loop control of the tissue temperature induced by the surgical instrument wherein a function of the temperature is used to determine when coagulation of tissue has occurred to a desired degree.

Although open loop energy instruments have been used successfully to control bleeding during surgical procedures, when such instruments are used, the primary control is the experience of the surgeon who responds to what is observed to be happening to the tissue as it is treated with energy. Often, particularly for endoscopic procedures, surgeons cannot readily see what is happening to the tissue. In addition, tissue properties may change quickly during energy delivery. A surgeon's reaction time may be insufficient for optimal efficacy. Consequently, the tissue treatment may not be as precisely controlled as may be desirable. Some problems that may occur include tissue charring, sticking of the tissue to the electrodes of the surgical instrument, and over or under treatment of the tissue.

Temperature-measuring devices have been described for use with tissue treating instruments to measure temperature and determine when the absolute temperature has exceeded a desirable temperature. These devices are typically used to signal to a user to turn off energy or to cause a control device to turn off or attenuate energy when the temperature has reached a level at which tissue sticking to the instrument may occur. Other instruments have used temperature feedback to maintain a set temperature to follow a predetermined temperature profile.

Notwithstanding these control arrangements, there is a continuing need for improvement in the control of heat energy delivery to the tissue and/or determination of when tissue treatment has reached an optimal level. In particular there is a need to provide a device and method for ultrasonic instruments that must perform both cutting and coagulating functions, and to provide closed loop feedback for separate cutting and coagulating aspects. This invention fulfills these needs.

SUMMARY OF THE INVENTION

The present invention is an ultrasonic surgical instrument incorporating a closed-loop feedback system that controls the energy delivered by the instrument into tissue. Accordingly, one embodiment of the present invention provides a temperature monitoring device and/or method which controls the tissue temperature at the end-effector of a therapeutic ultrasonic cutting and coagulating instrument as the tissue is being heated with ultrasonic vibrations from the instrument's end-effector. Based on a model of the behavior of tissue temperature (which may be inferred from instrument temperature) with the delivery of therapeutic energy, the monitored tissue (or instrument) temperature is used to control the coagulation phase, or the cutting phase, of tissue.

A temperature sensor is located at the end-effector, preferably on a clamping member. The temperature sensor measures the temperature of the tissue engaged by the end-effector either directly or indirectly. In the instrument, the temperature-measuring device may be in contact with the tissue or may indirectly measure temperature of the tissue by measuring the temperature of the end-effector. The temperature-measuring device preferably comprises a temperature transducer that changes the temperature measurement into a corresponding electrical signal indicative of the temperature at the temperature transducer. The signal from the temperature transducer is provided to feedback control circuitry and a device for selecting a function of the instrument for either cutting mode or coagulating mode.

When the temperature reaches the desired level for the selected function, indicating a desired tissue condition, a signal is provided to a control unit or the user, at which time the energy supply is switched off or attenuated. The feedback signal may, for example, provide a visual audible or tactile signal to a user, and/or may provide instructions to a control unit to automatically alter the energy supply to the tissue.

The energy source may be responsive to a power control signal of a controller. The feedback circuitry may be coupled to, or included with, the power controller. The power controller may include at least one electrical switch for selectively controlling the energy supplied to the instrument to coagulate tissue, or to cut tissue, depending on the electrical switch setting.

In accordance with another aspect of the present invention, a method of operating an apparatus for surgically heat treating tissue during surgical procedures is provided. Accordingly a preferred method comprises the steps of: selecting an operational mode of an ultrasonic surgical instrument, engaging tissue to be surgically treated with the end-effector of the ultrasonic surgical instrument; applying therapeutic tissue heating energy to the tissue to be treated; measuring the temperature of the tissue as it is being treated; generating a signal representative of the temperature of the tissue; and controlling the therapeutic tissue heating energy applied to the instrument in response to the temperature signal.

Another method of performing the present invention includes the steps of: supplying ultrasonic energy to tissue in the form of mechanical vibrations of an ultrasonic end-effector, supplying high-frequency electrical energy to tissue, measuring tissue electrical impedance, and altering the output of the ultrasonic generator in response to a measured tissue electrical impedance parameter.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIGS. 1a–1c are schematic illustrations of the assembly of a clamp coagulator accessory and an ultrasonic surgical instrument;

FIG. 3 is an enlarged fragmentary cross-sectional view of the distal end of the clamp coagulating accessory illustrating the cooperation of the ultrasonic surgical blade and a clamp jaw including a temperature transducer, the clamp jaw being illustrated in a jaw-open position;

FIG. 4 is a cross-sectional view thereof generally taken about on line 4—4 in FIG. 3;

FIG. 16 is an enlarged fragmentary cross-sectional view of the distal end of the clamp coagulating accessory illustrating the cooperation of the ultrasonic surgical blade and a clamp jaw including a plurality of temperature transducers, the clamp jaw being illustrated in a jaw-open position;

FIG. 17 is an enlarged view of the clamp arm illustrated in FIG. 16, showing placement of two temperature transducers within the clamp pad; and FIG. 18 is a bottom view of the clamp pad illustrated in FIG. 17.

DETAILED DESCRIPTION OF THE INVENTION

The present invention relates, in general, to a method and apparatus for controlling the heat treatment of tissue in response to the measured temperature as an indication of tissue treatment status of the tissue being treated by an ultrasonic cutting and coagulating instrument and, more particularly, to a method and apparatus for controlling the heat treatment of tissue in separate modes for ultrasonic cutting and ultrasonic coagulation.

Figure 2:
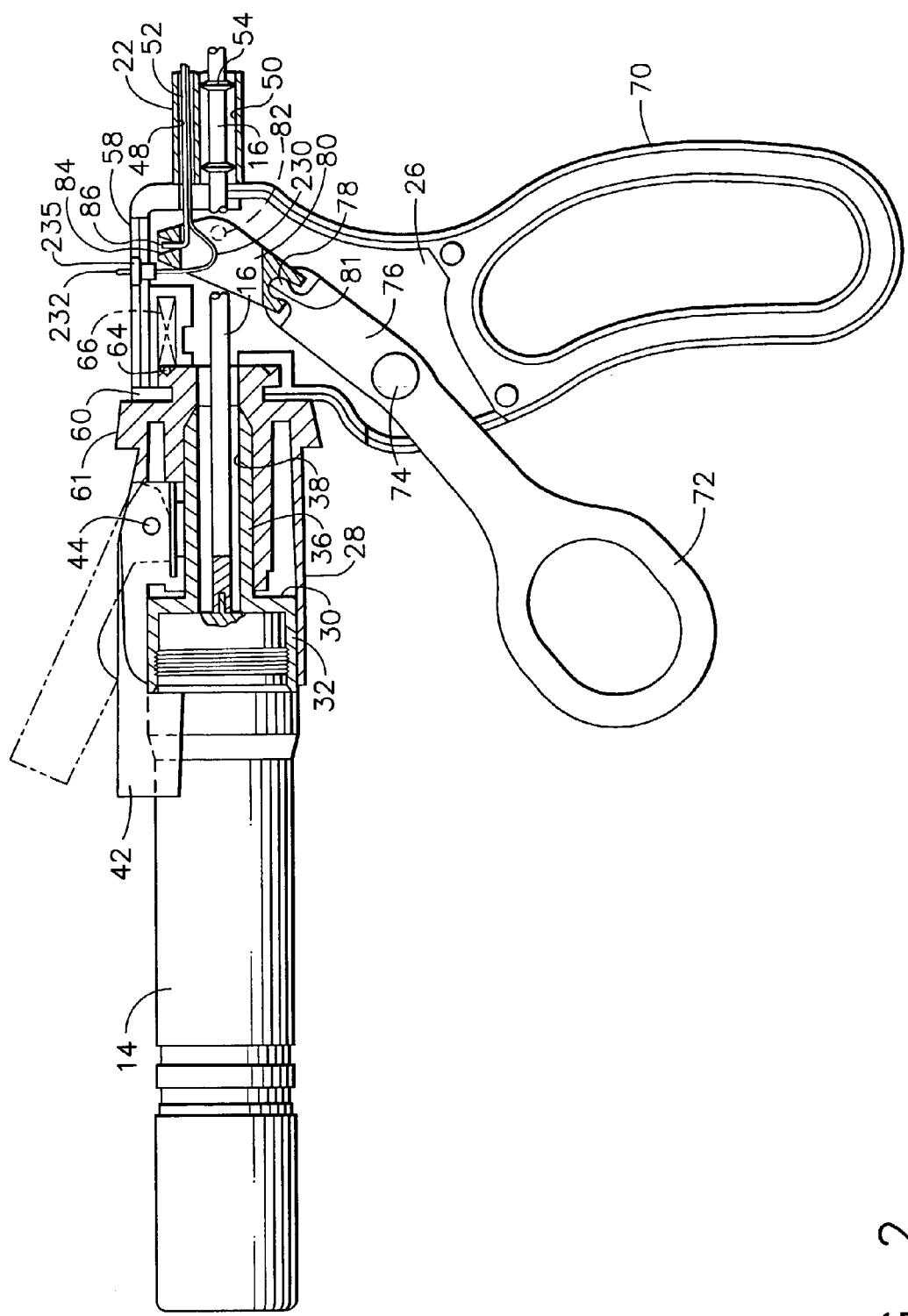
FIG. 2 is an enlarged fragmentary cross-sectional view illustrating the clamp coagulating accessory hereof secured to the hand-piece of the ultrasonic instrument.

Referring now to FIGS. 1a–1c, there is illustrated an ultrasonic surgical apparatus constructed in accordance with the present invention and including an ultrasonic surgical instrument, generally designated 10, and a clamp coagulator accessory, generally designated clamp coagulator 12. Ultrasonic ultrasonic surgical instrument 10 comprises a housing or hand-piece 14 housing a transducer, preferably a piezo-ceramic transducer, for converting an electrical signal, for example, a 55,000 Hz sinusoidal waveform, into a mechanical longitudinal vibration. With reference to FIGS. 1a and 2, ultrasonic surgical instrument 10 further includes an extension 16 having a blade coupler 18 screw-threaded to the distal end of extension 16, blade coupler 18 carrying a blade 20. The proximal end of extension 16, as illustrated in FIG. 2, is screw-threaded onto a stud projecting from one end of hand-piece 14 and connected to the transducer, whereby ultrasonic vibrations in a longitudinal direction are transmitted along extension 16 and blade coupler 18 to blade 20.

Clamp coagulator 12 includes a clamp assembly comprised of an elongated tube 22 pivotally carrying a clamp jaw 24 at its distal end and a clamp jaw 24 activation mechanism 26 at its proximal end. Clamp coagulator 12 also includes a clamp assembly mount 28 connected to the clamp assembly, as well as an adapter or nosecone 30. The nosecone 30 illustrated in FIGS. 1a and 2 is attached, preferably by screw-threading, to the end of hand-piece 14. The nosecone 30 comprises part of the clamp coagulator 12 to adapt ultrasonic surgical instrument 10 for use with the clamp coagulator 12.

In general, it will be appreciated that the blade coupler 18 can be connected directly to hand-piece 14 without the nosecone 30 and extension 16, and the ultrasonic surgical instrument 10 may be used for cutting and coagulating in a conventional manner. The clamp coagulator 12 may be disposed on the hand-piece 14 with or without the extension 16, depending upon the desired length of the surgical apparatus, and may be provided in different lengths for different surgical purposes. For endoscopic, particularly laparoscopic use, the extension 16 is applied to the hand-piece 14, and the clamp coagulator 12 includes the elongated tube 22 housing the extension 16. Thus, in the illustrated form, the clamp coagulator 12 is particularly adapted for laparoscopic use, although it will be appreciated that the clamp coagulator 12 may be provided with the hand-piece 14 for other surgical uses.

As illustrated, particularly in FIG. 2, the nosecone 30 of accessory clamp coagulator 12 includes an internally threaded cup-shaped housing 32 for threaded engagement with external threads 34 formed on the distal end of the hand-piece 14. Nosecone 30 also includes an axially extending sleeve 36 having a central bore 38. It will be appreciated that extension 16 extends through bore 38 for threaded connection with hand-piece 14. Clamp assembly mount 28 includes a generally cylindrical fitting 40 having an axial bore for receiving the sleeve 36 of nosecone 30. A lever 42 is pivotally mounted at lever mount 44 to fitting 40, lever 42 compressing a pad 46 for engagement along the outer surface of sleeve 36 to secure clamp coagulator 12 and the hand-piece 14 one to the other and prevent against longitudinal and rotational movement. Lever 42 operates as an over-center toggle and is thus pivotal between accessory mounting and demounting positions relative to hand-piece 14, as illustrated by the full and dashed lines in FIG. 2.

As further illustrated in FIG. 2, tube 22 has a pair of axial bores 48 and 50. Bore 48 carries an actuating rod 52 for actuating clamp jaw 24, as described in the ensuing description. When the clamp coagulator 12 is mounted to hand-piece 14, bore 50 receives the extension 16. As illustrated, extension 16 carries a plurality of longitudinally spaced rings, preferably formed of silicone, located at the node points of extension 16, to minimize or eliminate undesired transverse motion of the extension 16. The tube 22 is suitably fixed to the clamp activation mechanism 26.

Mechanism 26 includes scissors-like gripping handles or grips for pivoting the clamp jaw 24 between open and closed positions. Particularly, mechanism 26 includes a fixed finger handle or grip 70 and a thumb handle or grip 72 pivoted to housing 58 by pin 74. Thumb grip 72 is also fixed to a link 76 having a projecting knob 78 received in a corresponding slot 81 along the lower side of a generally annular ring 80. Ring 80 is mounted in housing 58 for pivotal movement about a generally transverse axis intersecting the longitudinal axis of the combined accessory and hand-piece 14. Suitable pins 82 are provided for pivotally mounting the ring 80 to housing 58 along its lateral sides. The upper portion of ring 80 includes an aperture 84 for receiving an upwardly bent end 86 of the actuator rod 52.

Figure 5:
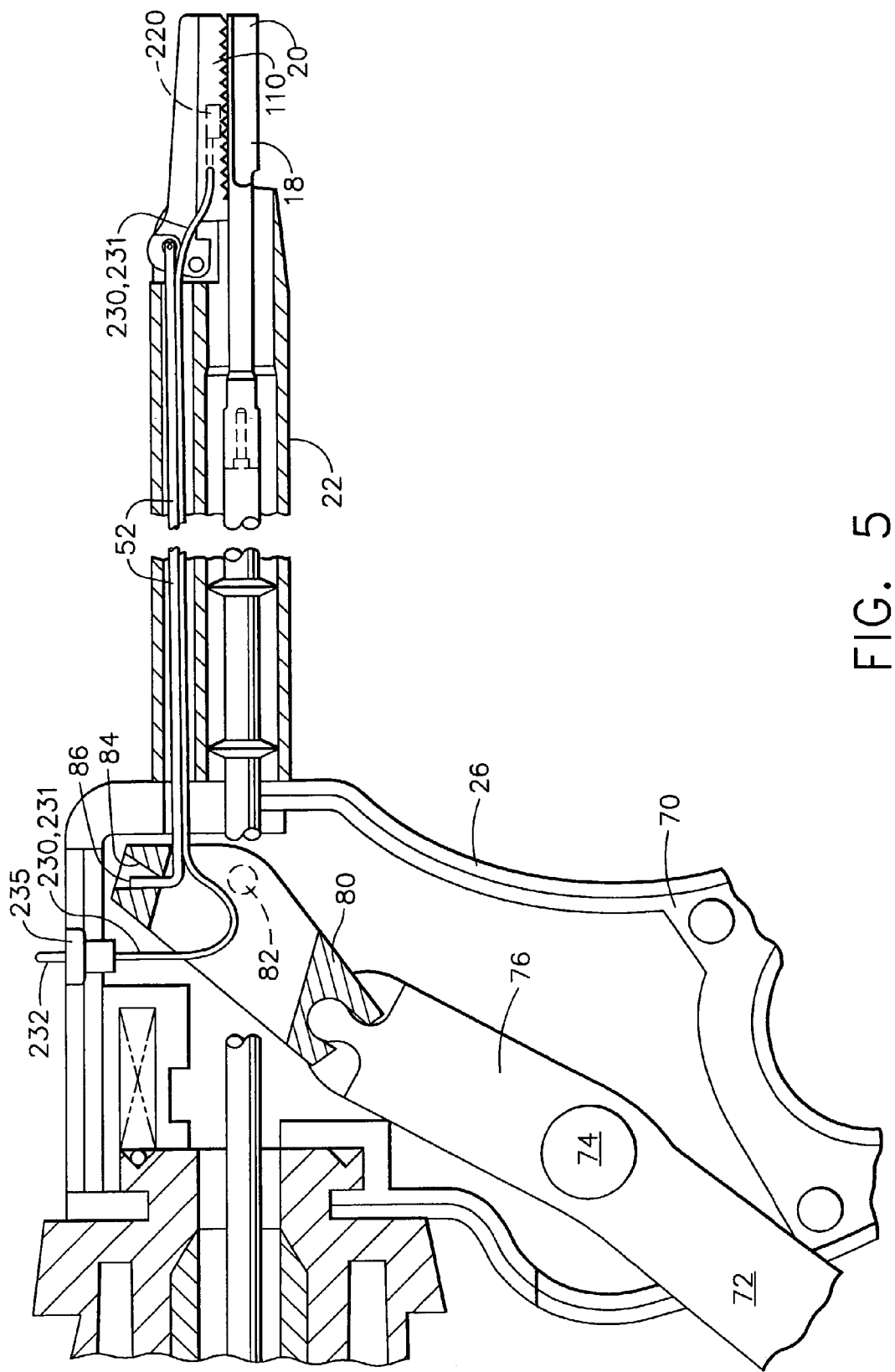
FIG. 5 is an enlarged fragmentary longitudinal cross-sectional view of the accessory with the clamp jaw illustrated in a closed position.

It will be appreciated from the foregoing and a review of drawing FIGS. 2 and 5, that pivoting thumb grip 72 toward finger grip 70 about pin 74 causes link 76 to pivot ring 80 in a clockwise direction, as illustrated in FIG. 2, with a substantial mechanical advantage. As will be appreciated from the following description, rotation of ring 80 in a clockwise direction displaces actuator rod 52 forwardly along tube 22 to pivot clamp jaw 24 into its closed position. Movement of thumb grip 72 in the opposite direction rotates ring 80 about pivot pins 82 in a counterclockwise direction, as illustrated in FIG. 2, to displace actuator rod 52 in the opposite direction, i.e., rearwardly, and hence pivot the clamp jaw 24 into its clamp open position. This clamp jaw 24 movement is indicated upon comparison of FIGS. 3 and 5.

Clamp jaw 24 is illustrated in FIG. 3 in a clamp open position and is pivotally attached to the actuator rod 52 adjacent the base 25 of the clamp jaw 24. The clamp jaw 24 is pivotally carried in a recess 23 on the end of tube 22 by a pin 90. It will be seen that, by advancing actuator rod 52 toward clamp jaw 24, clamp jaw 24 is pivoted in a clockwise direction about pivot pin 90 into the clamp closed position of FIG. 5 with the clamp pad 110, described hereinafter, bearing against the blade 20. Retracting movement of actuator rod 52 pivots the clamp jaw 24 in a generally counter-clockwise direction into the clamp open position illustrated in FIG. 3.

Figure 8:
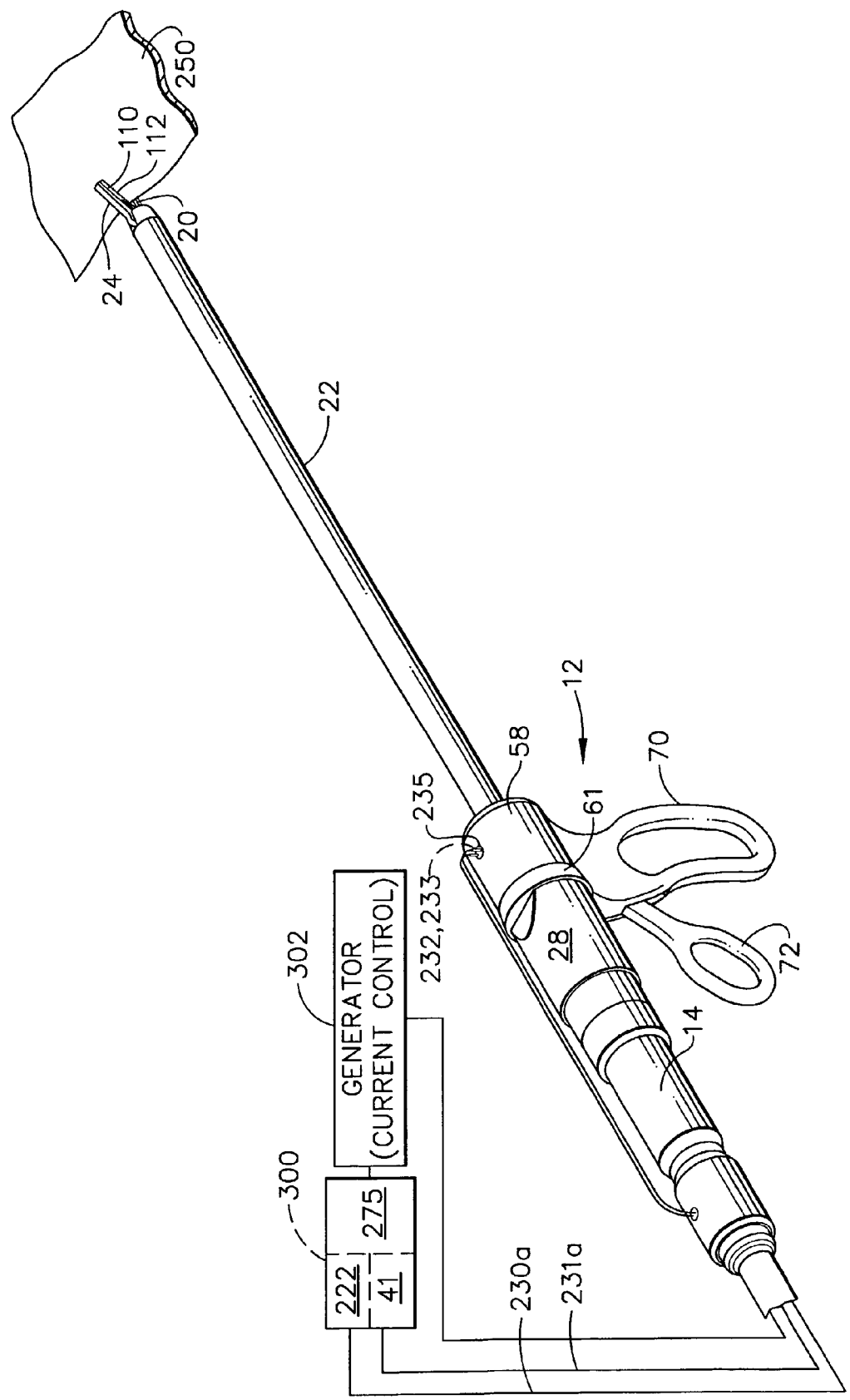
FIG. 8 is a partial perspective, partial schematic illustration of the temperature feedback device.
Figure 10A:
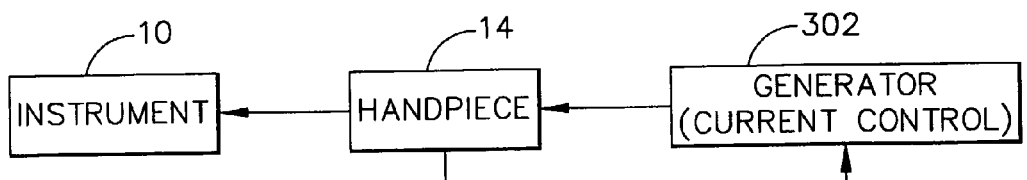
FIGS. 10-a and 10-b are block diagrams illustrating prior art and a block diagram in accordance with the present invention respectively.
Figure 10B:
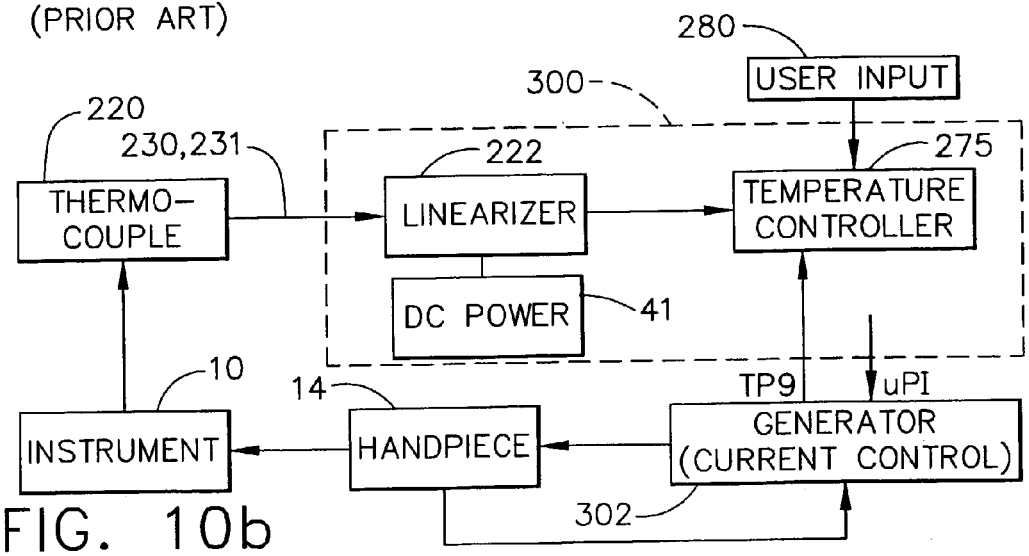

Referring to FIG. 5, clamp jaw 24 includes a temperature sensor 220 such as, for example, a 30 gage type K thermocouple. Conductors 230 and 231 connect temperature sensor 220 to thermocouple linearizer 222 as illustrated in FIGS. 8 and 10. Conductors 230 and 231 are disposed along actuator rod 52. Conductors 230 and 231 are routed through elongated tube 22 to plug connector 235, including contacts 232 and 233 (contact 233 hidden by contact 232), and then to thermocouple linearizer 222 (shown in FIGS. 8 and 10).

Referring now to FIGS. 3 and 4, because the blade coupler 18 is screw-threaded to the extension 16 or to the hand-piece 14 and blade couplers and extenders of different sizes are provided, an alignment guide is provided for obtaining rotational and longitudinal alignment of the accessory and the instrument when the accessory is applied to the instrument, to account for variations in the threaded dimensions, and to align the blade relative to clamp jaw 24. In one form of the alignment guide, there is provided a pin 98 that is receivable in a laterally extending aperture 100 in tube 22. When the blade coupler 18 is formed, it includes an enlarged diameter portion 102 having radiussed edges 104 (FIG. 3), and flats 106 extending from edges 104 formed along opposite sides thereof. By inserting the pin 98 through tube 22, and inserting the accessory over the extension 16 and blade coupler 18, ultrasonic surgical instrument 10 and clamp coagulator 12 can be manipulated such that rotational movement is prohibited by the engagement of the pin along one of flats 106. Longitudinal closing movement of the two parts is arrested by the engagement of the pin 98 along a radiussed edge 104.

Figure 6:
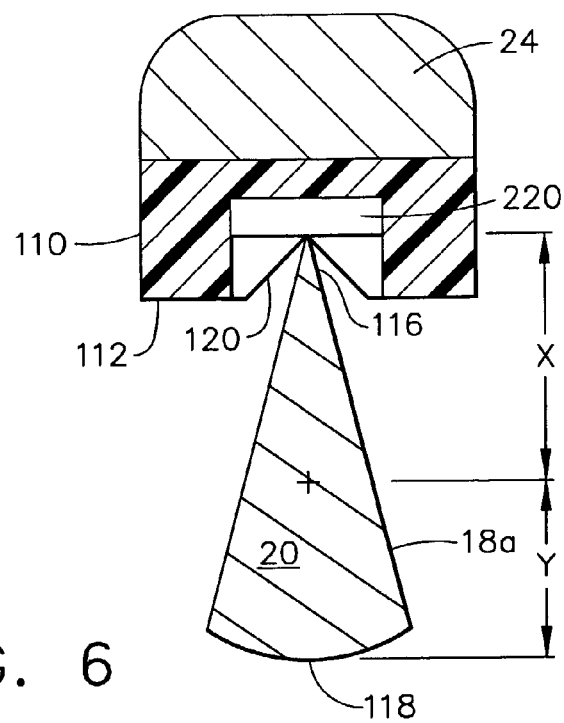
FIGS. 6 and 7 are schematic enlarged end elevation views of the cooperation between the clamp jaw and a multi-edged blade, the blade being illustrated in 180 degree apart orientations relative to the clamp jaw, respectively.
Figure 7:
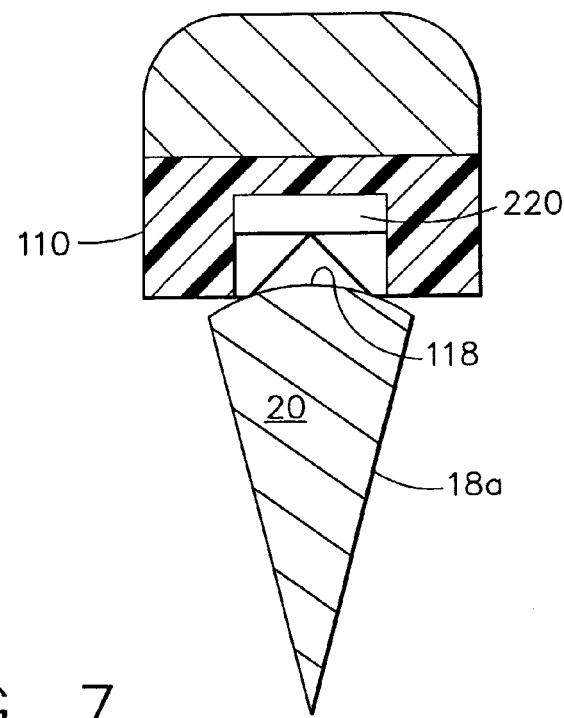

Referring now to FIGS. 3, 6 and 7, the clamp jaw 24 mounts a pad 110 for squeezing the tissue between the blade 20 and clamp jaw 24 against the side of the blade 20, to use the shearing action of the vibration to enhance tissue cutting/coagulating effects. Pad 110 is preferably formed of a polymeric or other compliant material and engages the blade edge when pivoted to its fully closed position. The use of compliant pad material prevents loud and annoying audible noise, which would occur if an ultrasonic blade were to contact a non-compliant (e.g., metallic) pad. Preferably, the pad is formed of a material having a low coefficient of friction but which has substantial rigidity to provide tissue-grasping capability, such as a polytetraflouroethelyne polymer, such as, for example, TEFLON®, trademark name of E. I. Du Pont de Nemours and Company. The pad 110 may be mounted to the clamp jaw 24 by an adhesive or mechanical fastener. Temperature sensor 220 is inserted into pad 10, and may be held in place through an interference fit, an adhesive, or other means known in the art.

Serrations 112 are formed in the clamping surface of pad 110 and extend perpendicular to the blade 20 axis to allow tissue to be grasped, manipulated, coagulated, and cut, without slipping from between the clamp jaw 24 and blade 20. While the clamp jaw 24 is pivoted within the recess 23 at the end of tube 22, the sides of the tube 22 are tapered to minimize obstruction of vision of the blade 20 and clamp jaw 24 by the tube consistent with the need to provide mechanical support for the clamp jaw 24. Additionally, it will be seen that the leading end of the tube 22 provides a tissue stop to prevent the tissue from entering the clamp coagulator clamp jaw 24 beyond the ultrasonically active region of the blade 20.

Referring now to FIGS. 6 and 7, there is provided a blade 20 having multiple blade edges which, when coupled with the ability to relatively rotate the blade 20 and clamp jaw 24, affords the surgeon the availability of more than one blade characteristic without replacing the blade 20 and the use of multiple blade edges with or without the clamp. For example, a preferred blade 20 design may comprise a generally triangular-shaped blade 20 in cross-section with two discrete edges, i.e., a narrow edge 116 to concentrate the ultrasonic energy enabling fast cutting/coagulating of unsupported tissue with clamping, and a broad edge or face 118 to create a wider zone of coaptive coagulation. As illustrated, the preferred shape of the broad face is a convex curve in a plane perpendicular to the direction of vibration. This concentrates the ultrasonic energy in the center of the clamp jaw 24 area and reduces the risk of shear cutting uncoagulated vessels at the blade 20 edge.

Pad 110 may include a groove, such as the V-shaped groove illustrated in FIG. 6, running the entire length of pad 110. Alternately, pad 110 may be flat, with or without serrations 112. With the substantially V-shaped groove 120 formed in the pad surface of the clamp jaw 24, the narrow edge 116 may be received in the apex of the groove. This enables the narrow blade 20 edge 116 to squeeze tissue with some shearing force in addition to the compressive clamping force. The groove 120 is preferably as deep or deeper than the depth of serrations so that the narrow blade 20 edge makes full pad contact along its length when the clamp jaw 24 is closed. Both the shearing action and the full-length contact aid in cutting thin tissue.

Referring now to FIGS. 1–4, to assemble the ultrasonic surgical instrument 10 and accessory clamp coagulator 12, the nosecone 30 is screw-threaded onto the end of hand-piece 14. The extension 16, with attached blade coupler 18, are then screw-threaded into the male stud projecting from the end face of hand-piece 14. Because the blade 20 is attached to the hand-piece 14 by a threaded joint, the angular orientation of the blade 20 relative to the hand-piece 14 is a variable. Because the clamp coagulator 12 is also oriented relative to the hand-piece 14, the initial angular orientation of the blade 20 relative to the clamp jaw 24 is also a variable. Further, the longitudinal position of the blade 20 tip relative to the clamp can also vary due to the requirement to manufacture each blade 20 assembly so that its length is an integer multiple of one-half the wavelength. Thus, the assembled blade 20 must be oriented rotationally and longitudinally to align with the clamp jaw 24. To accomplish this, the alignment pin 98 is passed through the aperture 100 in the tube 22 prior to attachment of the accessory and hand-piece 14 to one another. With the pin 98 in place, the accessory is telescoped over the blade coupler 18 and extender such that the blade coupler 18 and extender are received in the bore 50 of tube 22. By rotationally manipulating the accessory and instrument, the pin 98 will engage along a flat 106 of blade coupler 18. With further telescoping movement of the accessory and instrument, the blade coupler 18 radiussed edge 104 will engage against the pin 98. When this occurs, the accessory and hand-piece 14 are longitudinally and rotationally aligned, with the result that the blade 20 and clamp are aligned. Locking lever 42 is then pivoted to clamp the clamp coagulator 12 to hand-piece 14 to maintain that alignment. The alignment pin 98 is then removed. It will be appreciated that in the clamped condition, the clamp assembly mount and clamp assembly are detented in a selected rotational position relative to one another.

In using the device, with the accessory applied to the instrument as previously described, it will be appreciated that the clamp can be used to coagulate and cut with ultrasonic energy applied, can be used to grasp tissue without application of ultrasonic energy, can be used to coagulate/cut with the clamp jaw 24 open and tissue unclamped, can be used to probe or manipulate tissue without application of ultrasonic energy, and can be used, with the clamp jaw 24 closed, for blunt dissection. For example, when the clamp is used for coagulation/cutting, the clamp jaw 24 is opened by opening the finger and thumb grips 70 and 72, respectively. The desired blade 20 edge is then rotated to face the clamp jaw 24 surface. To accomplish that, the knob 61 can be rotated while holding the clamp assembly to thereby rotate the hand-piece 14, extension 16, blade coupler 18 and blade 20 relative to the clamp assembly including tube 22 and clamp jaw 24 into a position locating the selected blade 20 edge in opposition to the clamp jaw 24. The detent provided by the spring-biased ball 64 maintains this selected rotary alignment.

The apparatus may then be advanced so that tissue enters the space between the clamp jaw 24 and blade 20. A mode of operation may be selected, corresponding to a set temperature for a first operation, such as, for example, coagulation. A plurality of set temperatures may be available for specific tissue types, or procedures. The scissors-like grips are activated to close the clamp jaw 24 and ultrasonic power is applied. The longitudinal blade 20 vibration relative to the clamp jaw 24 couples to the tissue, causing coagulation, cutting or other desirable effects. When the device is advanced so that the blade 20 contacts the tissue, and ultrasonic power is applied, the blade 20 vibration couples to the tissue, causing optimized coagulation in a first operational mode, or optimized tissue cutting in a second operational mode, as will be described in more detail while referring to FIGS. 8,9,10-b, and 11.

Referring to FIGS. 5 and 8–11, there is illustrated an ultrasonic surgical instrument 10 having a temperature feedback device of the present invention. Referring to FIG. 8, the temperature sensor 220 is coupled to contacts 232 and 233 by way of conductors 230 and 231. An electrical energy supply 41 supplies a DC voltage to the sensor 220 through conductors 230a and 231a. Conductors 230a and 231a terminate in a plug connector 235, coupling energy source 41 and temperature monitoring circuitry 275 to the conductors 230 and 231. The conductors 230 and 231 are electrically isolated from each other and extend through elongated tube 22 and housing 58 to plug connector 235.

Conductors 230a and 231a are also coupled to thermocouple linearizer 222. The linearizer 222 includes current and voltage sensing means arranged to sense the current and voltage of the circuit including the temperature sensor 220 and conductors 230 and 231. Such sensing means are known in the art and typically include voltage and current transformers.

An electrical signal is coupled from conductors 230 and 231 of the temperature sensor 220 to the linearizer 222. The voltage across and current flowing through the temperature sensor 220 is sensed and used to determine the impedance of the temperature sensor 220 which is proportional to the temperature of the tissue 250. The temperature of the clamp pad 110 is proportional to the temperature of the tissue engaged between the clamp pad 110 and the blade 20.

Figure 9:
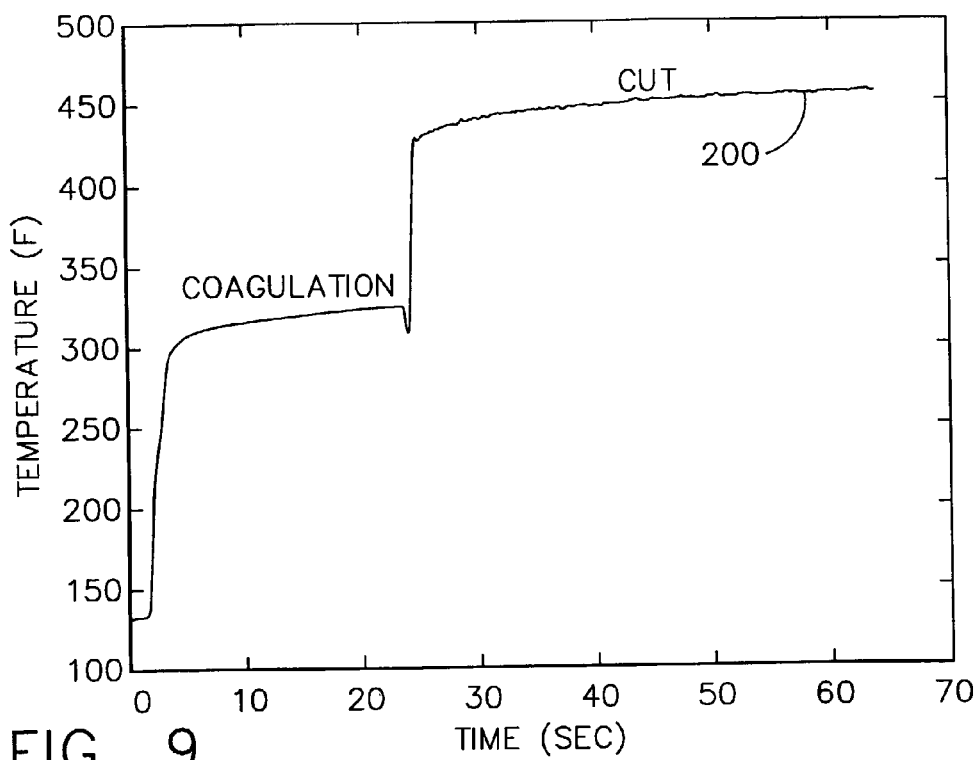
FIG. 9 illustrates a characteristic curve of temperature versus time of tissue being treated with the temperature feedback device.

Referring now to FIG. 9, a characteristic curve 200 of temperature vs. time using the ultrasonic surgical instrument 10 is shown. The curve represents the temperature of chamois with a first coagulate mode selected from approximately 0 to 22 seconds, and a second cut mode selected from approximately 22 to 65 seconds. In this example a coagulation temperature sensed by temperature sensor 220 of approximately 325 degrees F. was selected, and a cut temperature of approximately 450 degrees F. was selected. It was found from subsequent tissue testing that for this arrangement of instrument and thermocouple, coagulation was optimized between 158 and 300 degrees F., and cutting was optimized between 300 and 500 degrees F.

An audible, visible, tactile or other feedback system may be used to indicate when the selected temperature has been reached, and the operator can determine when sufficient cauterization has occurred. At this point, the operator may select another temperature for cutting purposes. One temperature can be set for coagulation and a second temperature for cutting of tissue. With the flip of switch 248 (see FIG. 11), the user can switch from the one temperature setpoint to the other.

Temperature control is implemented by an electronic circuit that adjusts input to the microprocessor of generator 302 of the ultrasonic surgical instrument 10 based on the temperature of the tissue being cut or coagulated. As the temperature rises to the desired value, the amount of current sent to hand-piece 14 is reduced. The oscillations generated in clamp coagulator 12 are reduced, thereby controlling the temperature of the tissue being cut or coagulated.

Figure 11:
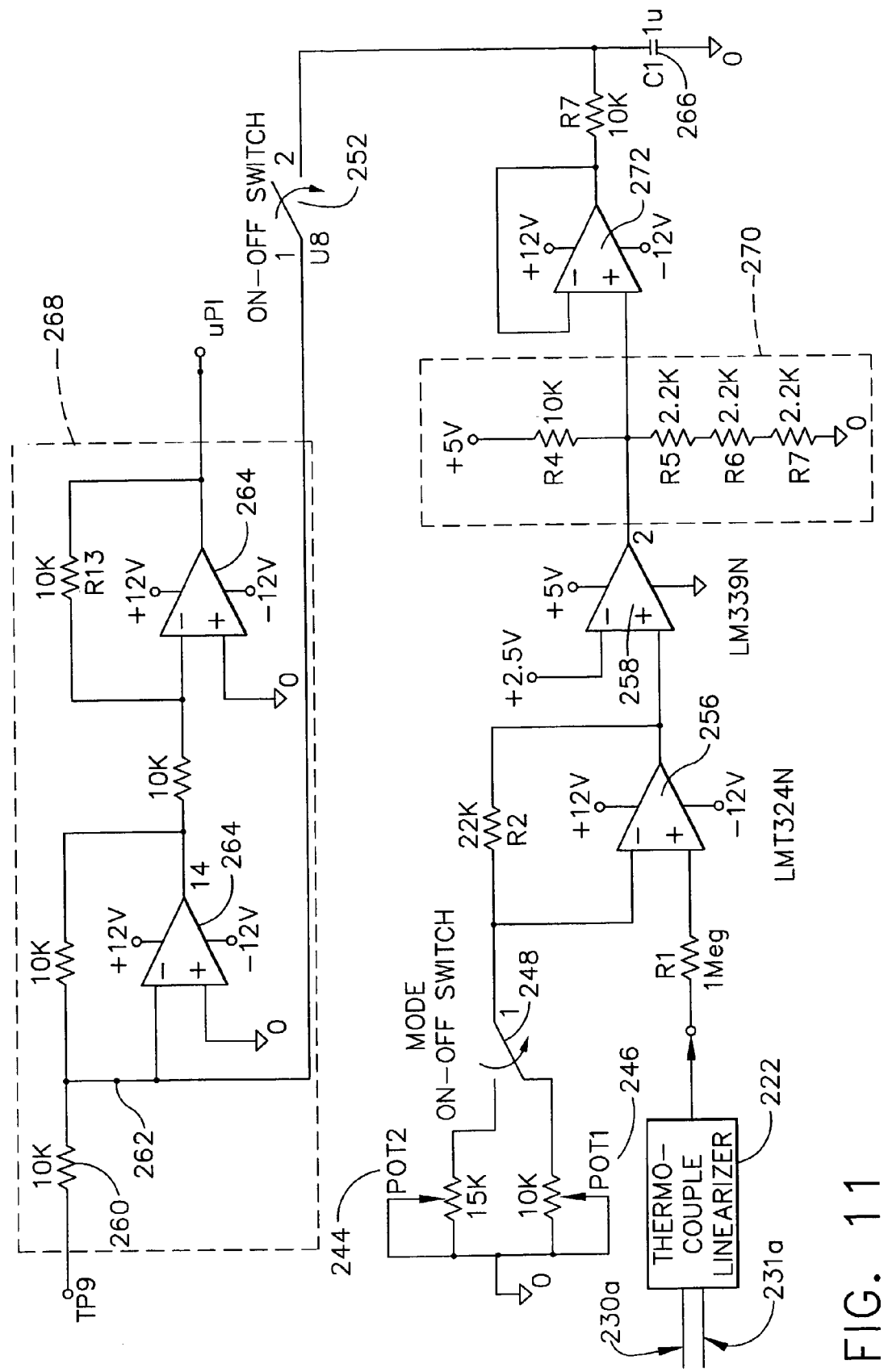
FIG. 11 is a circuit diagram for a control circuit in accordance with the present invention.

Temperature control of an ultrasonic system may be accomplished as illustrated in FIGS. 9, 10, and 11, utilizing additional functional control over an existing ultrasonic generator such as an ULTRACISION generator Model No. GEN01 available from Ethicon Endo-Surgery Inc., Cincinnati, Ohio. FIGS. 10-a and 10-b are the block diagrams of a prior art system and a system in accordance with the present invention, respectively. The excursion control system (sometimes also called the displacement control system) within the generator provides a constant current to the attached hand-piece 14 regardless of the load on the hand-piece 14. Different loads are produced at the hand-piece 14 when a cutting instrument is attached to the hand-piece 14, when that instrument is actually cutting, and when nothing is connected to the hand-piece 14. Throughout all these load changes, the generator maintains a constant current to the hand-piece 14.

The software within the generator's microprocessor specifically controls the amount of current sent to the hand-piece 14. The input to the microprocessor, which gives current information, is designated TP9 in FIGS. 10 and 11. TP9 connects to the microprocessor at the pin marked uP1 in FIGS. 10 and 11. The voltage at TP9 is proportional to the current at the hand-piece 14. At idle level, TP9 should equal 215 mV. At the maximum excursion available from the generator, level 5, TP9 should equal 2 Volts. Each excursion level has it's own corresponding ideal values represented at TP9.

The input to the microprocessor at uP1 is analyzed by the microprocessor and an output of zero Volts or +5 Volts is sent to the microprocessor output pin labeled uPC. An output of zero Volts occurs when more current needs to be sent to the hand-piece 14 and an output of 5 Volts means that currents should be cut off. By switching uPC between 5 Volts and zero Volts, the microprocessor can maintain a constant current at the hand-piece 14.

Constant temperature is also an important parameter because there are optimum temperature for the coagulation and cutting tissue. It would be desirable to be able to limit the current the hand-piece 14 can draw while maintaining a constant temperature during the cutting of tissue.

The circuit of FIG. 11 may be connected between TP9 and uP1 to add an additional temperature feedback function in accordance with the present invention. If the temperature at the cutting instrument is below the desired temperature, the temperature signal is zero Volts. If the instrument is above the desired temperature, the temperature signal is 2 Volts. The temperature signal is added to the voltage of TP9 and the summation of the two signals is the input to uP1. Whenever the temperature at the blade 20 of the instrument gets too high, the microprocessor will see an input that will be greater than 2 Volts and will stop sending current to the hand-piece 14.

Two potentiometers designated 244 and 246 in FIG. 11 allow the user to dial in two desired temperatures: preferably one for coagulating and one for cutting. An ON-ON toggle switch 248 allows the user to switch from coagulating temperature to cutting temperature while using the ultrasonic surgical instrument 10. An ON-OFF toggle switch 252 is used to turn the temperature control circuitry 275 on or off. With the temperature control circuitry 275 off, the system works similarly to the prior art instrument illustrated in FIG. 10-a, with no temperature control. In the on position, the ultrasonic surgical instrument 10 will heat the tissue no hotter than what the potentiometer dials indicate.

For an illustration of the temperature controlling circuitry 275, refer to FIG. 11. Note that the short circuit that exists between TP9 and uP1 in the prior art system illustrated in 10-a is broken to implement the present invention, and additional circuitry illustrated in FIG. 11 is inserted. Two chips were used in this design. One is an LM339N quad comparator 258 powered with +5 Volts and zero Volts. The other is a Motorola quad operational amplifier 259. Quad operational amplifier 259 is powered with a +/−12 Volts and has part number LMT324N.

A type K, 30 gage thermocouple 254 from Omega Engineering is used to sense the temperature of the tissue. The thermocouple 254 signal is fed into a linearizer 222 and the output is sent into an op-amp 256. The magnitude of signal amplification is determined by the potentiometers 244 and 246. Potentiometers 254 and 256 should be set in such a way that that output of the op-amp 256 is 2.5 Volts at the desired temperature input. The required resistance of potentiometers 244, 246 for a given desired temperature is $$Rpot = 22,000/((2.5/THERM) - 1)$$

Where THERM is the desired temperate in degrees Fahrenheit divided by 1000. Therefore 700° F. would correspond to THERM=0.700. The output of the first op-amp 256 is sent to an open collector comparator 258. If the op-amp 256 output is above 2.5 Volts, the measured temperature will be higher than the a desired temperature and the comparator 258 output will be:

6.6/(10+6.6)*5=1.99 V because of the voltage divider 270. If the first op-amp 256 has an output below 2.5 Volts, the comparator 258 has an ideal output of zero. In reality, the output will be related to the pull-up resistor 260. A high impedance pull-up resistor 260 will bring the low output closer to ground, but will also slow down the response time of the comparator 258. A one kilo-ohm pull-up resistor 260 yields a low output of 0.12 Volts. A ten kilo-ohm resistor 260 yields 50 mV. The signal is buffered before going into the summing junction 262 of the circuit of FIG. 11. A cascade of two inverting unity-gain op-amps 264 accomplishes the summation of the two signals.

The one uF capacitor 266 is added to enhance the temperature control performance. Without the capacitor 266, the thermocouple's 254 input into the summing junction could switch between zero Volts and 2 Volts at the slew rate of the buffering op-amp. Under these conditions, the temperature at the blade 20 of the ultrasonic surgical instrument 10 may oscillate with peak to peak amplitude of approximately 70 mV and a frequency of approximately one Hz. By adding capacitor 266, the input to the summing junction will ramp and decay with the RC time constant of the circuit. An electrolytic one uF capacitor 266 provided the best combination of minimal oscillations and fast response time.

Figure 12:
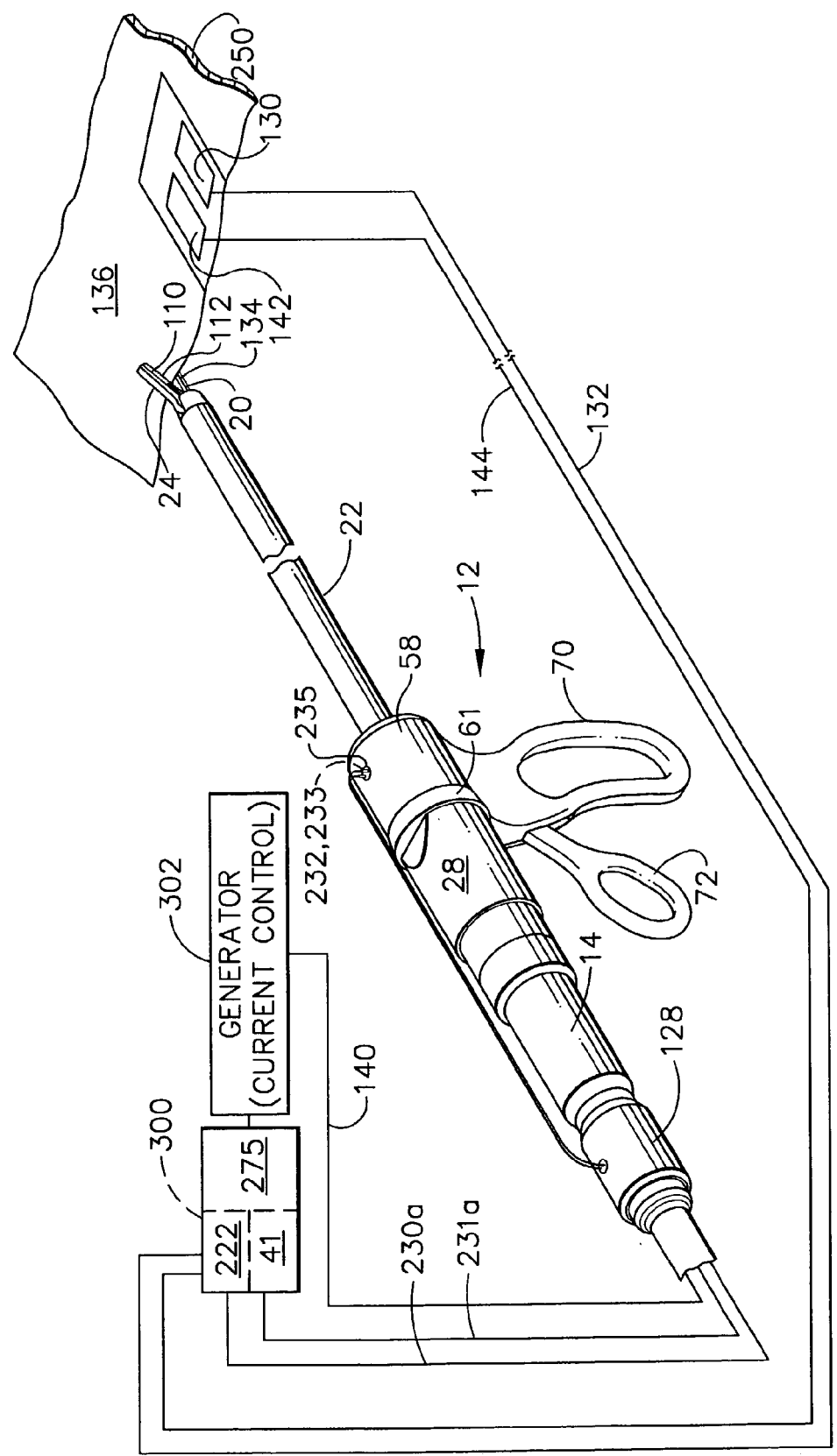
FIG. 12 illustrates an embodiment of the present invention utilizing a tissue electrical impedance monitor for active feedback control of an ultrasonic surgical system.

In a non-clamping ultrasonic surgical instrument 10, i.e. an instrument without a clamping jaw 24, an impedance feedback method may be preferable to the temperature feedback method described above. Referring now to FIG. 12, an embodiment of the present invention utilizing tissue electrical impedance for active feedback control includes generator 302, hand-piece 14, ultrasonic blade 20, a cable 128 encompassing a send wire 140, a send electrode 134, a return electrode 130, and a return wire 132. Tissue 136 completes the electrical path from send electrode 134, through tissue 136, to return electrode 130. It may be advantageous to provide a plurality of return electrodes to feed back information to generator 302 such as, for example, an optional return electrode 142, and an optional return wire 144.

Figure 13:
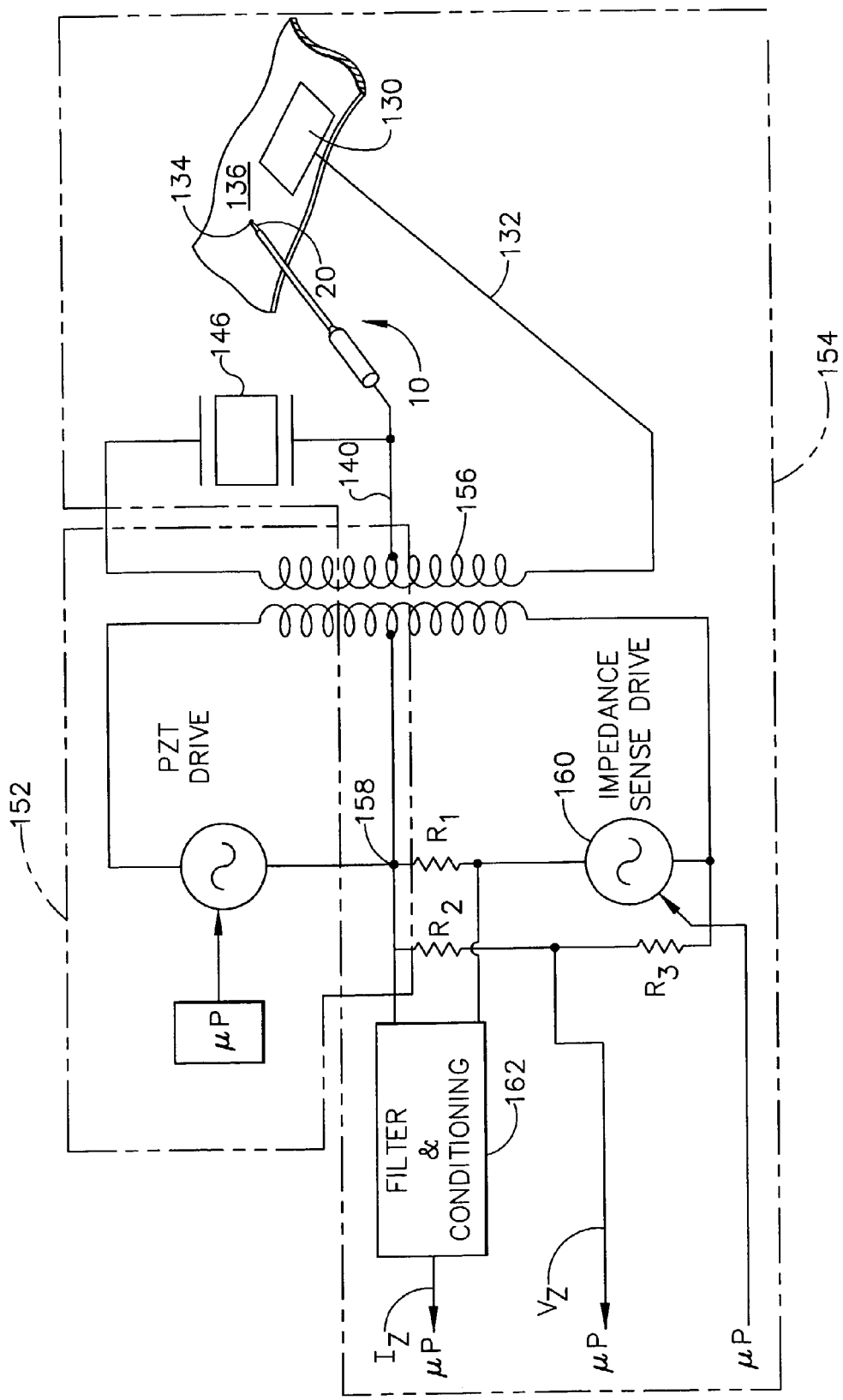
FIG. 13 is a circuit diagram illustrating one means of providing electrical impedance feedback to an ultrasonic surgical system.

The schematic of FIG. 13 illustrates one method of implementing electrical impedance feedback control to ultrasonic generator 302. In the schematic of FIG. 13, a microprocessor used to control an impedance feedback signal processing device is generally designated as microprocessor µp. A current signal is designated as $I_z$ and a Voltage signal is designated as $V_z$. As is known in the art, current $I_z$ or Voltage $V_z$ sensing could alternately be accomplished through resistive or inductive sensing means.

The ultrasonic portion 152 of the circuit diagram illustrates an ultrasonic generator such as, for example, generator 302. The electrical impedance portion 154 of the circuit is the impedance sensing device, used to provide a high frequency sensing current $I_z$ that can be used to detect the presence, absence, and condition (impedance) of tissue being treated by ultrasonic blade 20. The circuit diagram also shows a novel approach of utilizing a center tapped isolation transformer 156 to reference both the ultrasonic portion 152 and electrical impedance portion 154 to a common reference potential 158. By utilizing this common referencing approach the system has the advantage, in it's simplest case, of adding only one additional wire (return wire 132) to the output of conventional ultrasonic generators. Referencing voltage potentials between ultrasonic generator portion 152 and impedance feedback signal processing device 150 need not be accomplished via center tapping of isolation transformer 156, but could be done with other means such as, for example, discrete transformers. As is known in the art, adding a number of wires to the return electrode 130 system could be used for the purpose of determining return electrode 130 contact integrity.

On the primary side of isolation transformer 156, in electrical impedance portion 154, is a signal source 160 capable of generating a low current, high frequency (>300 kHz), AC signal. This common referenced signal is coupled through the isolation transformer 156 to the return electrode 130. The drive frequency of the electrical impedance portion 154 is selected to avoid any excitation of hand-piece 14 harmonics, as well as avoid "noisy" areas in the frequency spectrum that would cause errors in the measurement of sense current $I_z$.

The impedance sense current $I_z$ flows on the isolation transformer 156 secondary through the return wire 132 and return electrode 130, which is attached in the same manner as in electrosurgery, through the tissue 136 being ultrasonically treated, and back down ultrasonic blade 20 to the isolation transformer 156. The impedance sense current $I_z$ is then measured as a voltage drop across $R_1$. Alternatively the current $I_z$ could be measured by replacing $R_1$ with a current sensing transformer. The voltage developed across $R_1$ is then connected to an optional AC filtering and conditioning circuit 162 to filter out frequency components outside the range of the electrical impedance portion 154, and condition the current $I_z$ signal for analog-to-digital (A/D) conversion by the microprocessor µp. Similarly, the voltage $V_z$ produced by the electrical impedance portion 154 is sampled by the voltage divider $R_2/R_3$ and sent to the microprocessor µp for A/D conversion.

Once the microprocessor µp has available the voltage $V_z$ and current $I_z$, the tissue impedance can be calculated as the ratio of $V_z/I_z$. With tissue impedance information many possible control schemes can be implemented such as, for example, automatic tip excursion reduction, automatic on/off control, and tip excursion modulation.

Automatic tip excursion reduction reduces the tip excursion of blade 20 when no tissue 136 is present. When tissue 136 is being treated, impedance is measured which is below a predetermined threshold. Tip excursion is maintained while tissue 136 is present. Once impedance rises above the threshold, indicating that tissue 136 is no longer in contact with blade 20, tip excursion is reduced to prevent undesirable damage to the blade 20.

Automatic on/off control is similar to auto-bipolar mode on some electrosurgical generators, when using a blade 20 type instrument, tip excursion is automatically ramped up to a set point when tissue 136 contact is detected. When tissue 136 is no longer detected, tip excursion is ramped back down.

Tip excursion modulation uses the sensed tissue impedance signal to modulate blade 20 tip excursion, maximizing the effectiveness of coagulation and cutting. For example, to maximize the effectiveness of blade 20 to cut and coagulate, start blade 20 tip excursion at a lower level until a predetermined change in impedance is detected, and then ramp up blade 20 tip excursion to transect the tissue. Once the tissue separates, as detected by a rapid rise in impedance, reduce the blade 20 tip excursion back down to prevent unwanted damage to the blade 20.

Figure 14:
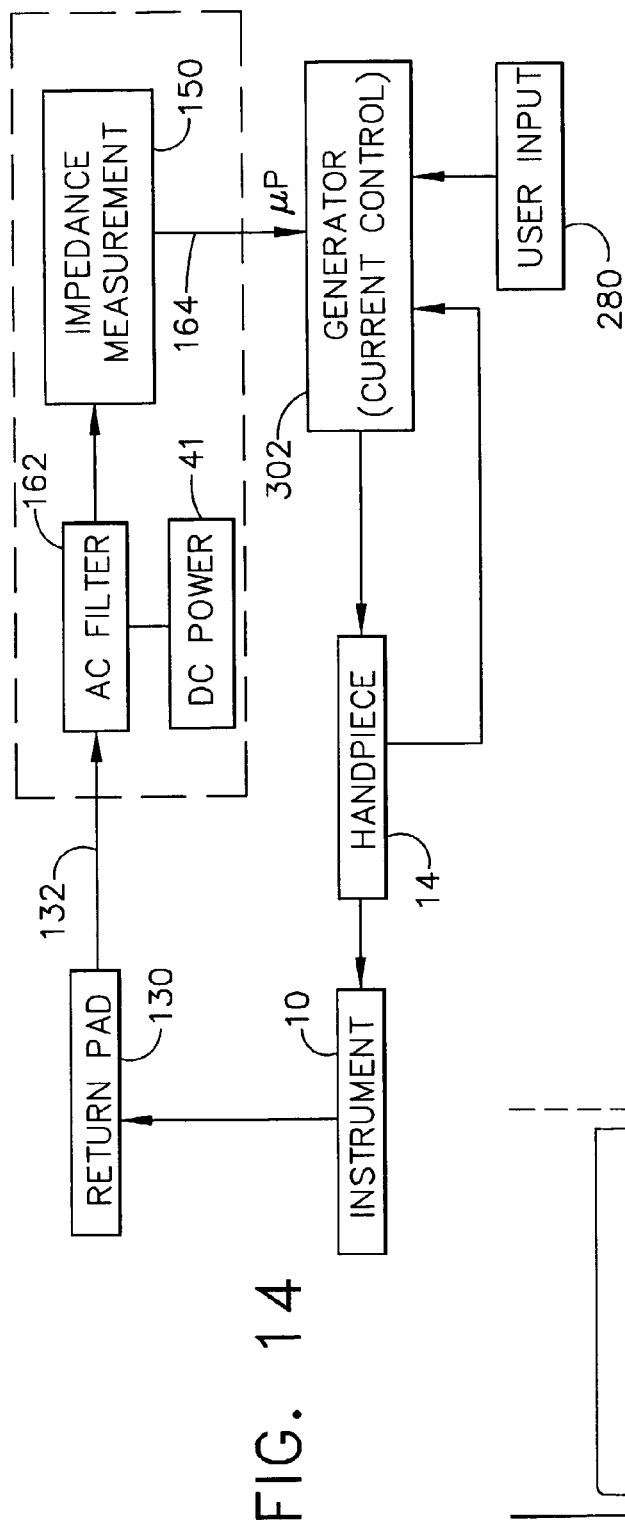
FIG. 14 is a block diagram illustrating the control scheme for an embodiment of the present invention utilizing a tissue electrical impedance monitor for active feedback control of an ultrasonic surgical system.

FIG. 14 illustrates a method of implementing impedance control into an ultrasonic surgical system. User input 280 is provided to the generator 302 in the form of, for example, stepping on a foot-switch. Generator 302 sends two electrical signals to hand-piece 14, one to activate the ultrasonic transducer, and the other to provide a high-frequency electrical signal to ultrasonic surgical instrument 10. Ultrasonic surgical instrument 10 performs a surgical procedure on tissue such as, for example, cutting or coagulation. Simultaneously, return electrode 130 receives the high-frequency electrical signal transmitted through the tissue from ultrasonic surgical instrument 10. An optional conditioning circuit 162 provides current $I_z$ and voltage $V_z$ signals to impedance feedback signal processing device 150. Impedance feedback signal processing device 150 derives an action signal 164 indicative of a desired action for generator 302 such as, for example, turn on, turn off, modify output excursion, modify output frequency, or the like. Generator 302 then acts on action signal 164 by either performing the desired action, or notifying the user of the action signal 164.

Figure 15:
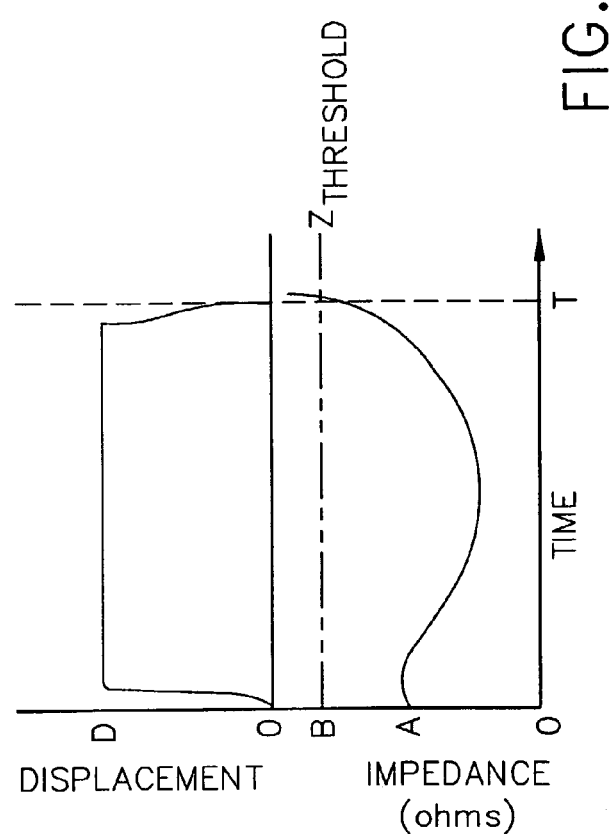
FIG. 15 graphically depicts one embodiment of utilizing active electrical impedance feedback to an ultrasonic surgical system to turn the system off when an electrical impedance threshold is reached.

FIG. 15 illustrates one potential action scenario graphically. The graphs plot potential blade 20 tip excursion and measured electrical impedance on the abscissa against time on the ordinate. At time 0 user input 280 turns on generator 302. A tissue path electrical impedance A is measured at time 0. A tissue path electrical impedance B was predetermined as a generator 302 turn-off action initiation. Blade 20 excursion starts from zero at time 0 and increases to excursion D, where it is maintained until time T. At time T the tissue path electrical impedance reaches electrical impedance B, sending action signal 164 to generator 302. Generator 302 then turns off automatically, thereby reducing blade 20 tip excursion from D back down to zero.

FIGS. 16–18 illustrate yet another embodiment of the present invention utilizing a plurality of temperature transducers for active feedback control of an ultrasonic generator 302. Clamp jaw 24 is illustrated in FIG. 16 in a clamp open position as was shown earlier in FIG. 3. In FIGS. 16–18 clamp jaw 24 now includes a plurality of temperature sensors (temperature sensor 220 and a temperature sensor 295 illustrated) such as, for example, 30 gage type K thermocouples. Conductors 230 and 231 connect temperature sensor 220 to thermocouple linearizer 222 as illustrated in FIGS. 8 and 10. A second set of conductors, conductors 290 and 291 are disposed along actuator rod 52 and connect temperature sensor 295 to thermocouple linearizer 222 similarly to conductors 230 and 231. Conductors 290 and 291 are also routed through elongated tube 22 to plug connector 235, which would now include four contacts for a two-thermocouple system.

FIGS. 17 and 18 illustrate the arrangement of temperature sensors 220 and 295 to provide heat flow and temperature difference information to generator 302 from ultrasonic surgical instrument 10. Temperature sensors 220 and 295 are separated axially, spaced different distances from blade 20. Temperature sensor 295 is illustrated closer to blade 20, and temperature sensor 220 is illustrated further from blade 20. In this arrangement, as heat flows into clamp pad 110, temperature sensor 295 will register the heat before temperature sensor 220. This temperature differential may be measured and provide heat flow information to generator 302. In a preferred embodiment, slots 296, 297, 298, and 299 reduce heat flow into temperature sensors 220 and 295 from lateral directions, providing a more accurate indication of heat flow into clamping jaw 24 from the tissue being treated.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An ultrasonic surgical instrument comprising:
    an ultrasonic transmission member having a proximal end and a distal end;
    an ultrasonically actuated blade located at the distal end of the transmission member, wherein the blade comprises a tissue contacting surface;
    a clamp member supported adjacent the blade and comprising a clamp pad, the clamp pad comprising:
        a first temperature-measuring device arranged to produce a first signal representative of a first measured temperature;
        a second temperature-measuring device arranged to produce a second signal representative of a second measured temperature; and
    a signal processing device arranged to receive said first and second signals, said signal processing device generating a control signal for controlling said ultrasonic surgical instrument.

2. The ultrasonic surgical instrument of claim 1, wherein said signal processing device derives a difference signal indicative of the temperature difference between said first temperature-measuring device and said second temperature-measuring device.

3. The instrument of claim 2 wherein said signal processing device compares said difference signal to a first predetermined signal level and provides said control signal to maintain said ultrasonic surgical instrument near said first predetermined signal level.

4. The instrument of claim 3 wherein said ultrasonic surgical instrument further includes a second predetermined signal level.

5. The instrument of claim 4 wherein said signal processing device maintains said ultrasonic surgical instrument near said first predetermined signal level in a first functional mode and said signal processing device maintains said ultrasonic surgical instrument near said second predetermined signal level in a second functional mode.

6. The instrument of claim 5 wherein said first functional mode is coagulating and said second functional mode is cutting.

7. The instrument of claim 6 wherein said ultrasonic surgical instrument further comprises a plurality of slots surrounding said first and second temperature sensing devices.

* * * * *